(12) United States Patent
Lih

(10) Patent No.: US 10,052,115 B2
(45) Date of Patent: Aug. 21, 2018

(54) CHOKING INTERVENTION DEVICE AND METHOD OF USE THEREOF

(71) Applicant: Arthur Lih, Springfield Gardens, NY (US)

(72) Inventor: Arthur Lih, Springfield Gardens, NY (US)

( * ) Notice: Subject to any disclaimer, the term of this patent is extended or adjusted under 35 U.S.C. 154(b) by 1043 days.

(21) Appl. No.: 14/264,590

(22) Filed: Apr. 29, 2014

(65) Prior Publication Data

US 2015/0190158 A1    Jul. 9, 2015

Related U.S. Application Data

(60) Provisional application No. 61/925,460, filed on Jan. 9, 2014.

(51) Int. Cl.
| | |
|---|---|
| *A61B 17/24* | (2006.01) |
| *A61B 17/50* | (2006.01) |
| *A61M 16/00* | (2006.01) |
| *A61M 16/06* | (2006.01) |
| *A61M 1/00* | (2006.01) |
| A61B 17/30 | (2006.01) |

(52) U.S. Cl.
CPC ............ *A61B 17/24* (2013.01); *A61M 1/0066* (2013.01); *A61M 1/0072* (2014.02); *A61M 16/0009* (2014.02); *A61M 16/0075* (2013.01); *A61M 16/06* (2013.01); *A61B 17/50* (2013.01); *A61B 2017/306* (2013.01); *A61M 2205/075* (2013.01)

(58) Field of Classification Search
CPC .............. A61M 16/0075; A61M 16/06; A61M 16/0009; A61M 1/0072; A61M 2205/075; A61B 17/24; A61B 17/50; A61B 2017/306; E03D 11/00

USPC .......................................................... 606/106
See application file for complete search history.

(56) References Cited

U.S. PATENT DOCUMENTS

| | | | |
|---|---|---|---|
| 3,316,903 A | 5/1967 | Richards | |
| 3,939,830 A | 2/1976 | da Costa | |
| 4,768,237 A | * 9/1988 | Torti | ..................... E03C 1/308 |
| | | | 4/255.05 |
| 4,934,360 A | 6/1990 | Heilbron et al. | |

(Continued)

FOREIGN PATENT DOCUMENTS

| | | |
|---|---|---|
| CH | 399 657 | 2/1963 |
| DE | 230740 | 3/1910 |

(Continued)

OTHER PUBLICATIONS

Search Report dated Aug. 21, 2015 for International Application No. PCT/US15/22731.

*Primary Examiner* — Christopher L Templeton
*Assistant Examiner* — George J Ulsh
(74) *Attorney, Agent, or Firm* — Duane Morris LLP

(57) ABSTRACT

A choking intervention device for clearing an object obstructing a breathing passage of a choking victim includes a bellows assembly and a removable facemask configured to enclose a person's mouth and nose. The bellows assembly includes a bellows having a base with an opening thereon. The opening is configured to provide access to an interior volume of the bellows assembly. The bellows assembly further includes a handle on the bellows at a side opposite the base. The facemask is coupled to the base of the bellows and is configured to enclose the choking victim's mouth and nose.

18 Claims, 4 Drawing Sheets

(56) References Cited

U.S. PATENT DOCUMENTS

| | | | |
|---|---|---|---|
| 4,971,053 | A | 11/1990 | Tarrats |
| 5,313,938 | A | 5/1994 | Garfield et al. |
| 5,609,149 | A | 3/1997 | Takach |
| 5,782,837 | A | 7/1998 | York |
| 6,478,770 | B1 | 11/2002 | Litkouhi et al. |
| 7,351,245 | B2 | 4/2008 | Rozinsky et al. |
| D613,468 | S | 4/2010 | Kosasih et al. |
| 2003/0028158 | A1 | 2/2003 | Litkouhi et al. |

FOREIGN PATENT DOCUMENTS

| | | |
|---|---|---|
| FR | 668573 | 11/1929 |
| FR | 746185 | 3/1933 |
| WO | WO-2007/073211 A1 | 6/2007 |
| WO | WO 2012/091949 | 7/2012 |

\* cited by examiner

CHOKING INTERVENTION DEVICE AND METHOD OF USE THEREOF

RELATED APPLICATION

The present application claims priority of provisional patent application No. 61/925,460 filed Jan. 9, 2014, the contents of which are incorporated herein in their entirety.

FIELD OF THE INVENTION

The present disclosure generally relates to first aid devices, and more specifically to a device for removal of an object obstructing an airway.

BACKGROUND OF THE DISCLOSURE

Choking (i.e., the unintentional obstruction of the respiratory tract by inhalation of ingestion of a foreign object) is one of the leading causes of accidental death in children. In one estimate, approximately 4,000 individuals in the United States die every year due to choking, making it one of the top five causes of death in the United States. In the year 2000 alone, 160 children 14 years or younger died from choking. For every choking death, there are more than 100 visits to emergency departments for choking incidents. According to the Centers for Disease Control and Prevention (CDC), an estimated 17,537 children 14 years and younger were treated for choking in an emergency department, in 2001 alone.

Choking may or may not fully block the respiratory tract. In cases where the respiratory tract is fully blocked, or blocked sufficiently to impair breathing, every minute a child is choking can diminish the chances of full recovery. For example, if the obstruction is removed and the child is able to breathe normally within 4 minutes, brain damage is unlikely. On the other hand, when the brain is without oxygen for 4 to 6 minutes, brain damage is possible. Brain damage becomes probable when the brain is deprived of oxygen for 6 to 10 minutes. If the oxygen deprivation exceeds 10 minutes, brain death is likely.

In view of the foregoing, first aid should be administered as soon as possible to avoid brain damage and death. However, many people who witness a choking situation may not be familiar or proficient with first aid treatments. For example, the Heimlich maneuver, in which a second individual performs abdominal thrusts to the victim's torso below from behind the body and beneath the rib cage to create pressure in the lungs to possibly expel the obstructing object, is not known by many. For over 100 million individuals in the United States, the Heimlich maneuver may not even be an option due to various factors, such as: disability, pregnancy, obesity, or simply being alone.

The victim many also not be able to be moved into a proper position for the Heimlich maneuver due to weight or the environment they are in. The Heimlich may also fail because the victim may lack sufficient air in the lungs to develop enough pressure to expel the object. For example, the victim may have ingested the obstructing object immediately upon completing an exhaling step in the breathing cycle or have already exhaled the air by coughing.

For such situations, a source of suction to expel the object from the victim's throat would be a better solution. Instead, critical time is typically wasted for emergency medical personnel to arrive to the scene, which is often too late to prevent permanent damage or death.

Although choking intervention devices are known in the art, they are generally complex in that they include many parts. Such complexity not only increases the overall cost but also makes prior art devices less reliable in that more components could fail. Indeed, prior art devices typically are piston driven and have rubber seals for the piston, where the seals degrade over time, thereby limiting the effectiveness of the tool. Thus, after years of storage, such prior art devices may fail to provide proper suction because of the degradation of the seals. Further, many prior art choking intervention devices require mounting and are therefore not truly portable, thereby limiting their range of use. Keeping them in a glove compartment of a vehicle or in a picnic basket may not be a convenient option.

Accordingly, it would be beneficial to have a simple and effective way to clear the airwaves in an emergency situation. It would be also beneficial to have a device and method that is cost effective, reliable, and does not degrade over time. It would be further beneficial to have a device and method that does not rely for help on a second party in a choking emergency situation.

SUMMARY OF THE DISCLOSURE

In one embodiment a choking intervention device includes a bellows assembly and a removable facemask that is configured to enclose a person's mouth and nose. The bellows assembly further includes a bellows, which has a base with an opening formed thereon and a handle provided on the bellows at a side opposite the base.

In one embodiment, the facemask further includes a seal configured to provide a seal between the facemask and a face when the facemask is placed over the person's mouth and nose.

In one embodiment, the facemask further comprises a connector configured to slidingly insert into the opening on the base of the bellows. The connector is further configured to provide fluid communication between the interior volume of the bellows and the facemask.

In one embodiment, the bellows assembly and the facemask are a single piece of polymer constructed via injection molding.

In one embodiment the bellows assembly and the facemask are two separate pieces. The facemask is removable from the bellows assembly between the opening and the connector.

In one embodiment, the bellows assembly is configured to couple to different size face masks. For example, the different face masks may be dimensioned in discrete sizes (e.g., small, medium, large, extra-large) to better accommodate the mouth and nose of the choking victim. In other another embodiment, the facemask is configured to be of universal size.

In one embodiment, the choking intervention device further includes at least one relief valve configured to allow air to escape from inside the bellows assembly when the bellows is being compressed and prevent air from entering the bellows assembly when the bellows is being expanded, when the facemask is positioned over the victim's mouth and nose. For example, the relief valve may be disposed on at least one of (i) the bellows assembly and (ii) the facemask.

The bellows is configured to be compressed when the handle is pushed towards the victim's mouth and nose, and to expand to create a pressure differential between a throat and an esophagus of the victim when the handle is pulled away from the victim's mouth and nose.

The choking intervention device is portable and does not need to be mounted. It can be used by the choking victim themselves during a choking emergency.

Also discussed is a method of clearing an object obstructing a breathing passage of a choking victim using a device comprising a bellows assembly and a facemask coupled the bellows. The choking victim's mouth and nose with the facemask is enclosed. A handle on the bellows assembly is pushed towards the choking victim's mouth and nose. The bellows of the bellows assembly is thereby compressed.

A seal is provided between the facemask and the face (i.e., mouth and nose) of the victim. Fluid communication is provided between an interior volume of the bellows and the facemask. Air is allowed to escape from inside the bellows assembly when the bellows is being compressed.

The handle is then pulled away from the victim's mouth and nose. Outside air (e.g., outside the chamber created between the choking intervention device and the victim) is prevented from entering the bellows assembly when the bellows is being expanded by the unidirectional release valve.

The bellows is expanded and a pressure differential created between the throat and the esophagus of the victim by pulling the handle away from the victim's mouth and nose. The obstructing object is thereby dislodged from the breathing passage of the choking victim. The steps can be repeated several times until the breathing passage is cleared.

BRIEF DESCRIPTION OF THE DRAWINGS

These and other features, aspects, and advantages of the present invention will become better understood with regard to the following description, appended claims, and accompanying drawings, wherein:

DETAILED DESCRIPTION

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

The various examples disclosed herein generally relate to first aid devices and more particularly to devices and methods for removal of an object obstructing an airway. The choking intervention devices described herein are used for clearing an object obstructing a breathing passage of a choking victim. The victim's mouth and nose is enclosed with the choking intervention device to provide a seal between the device and the victim. When a handle of the choking intervention device is pulled away from the victim's mouth and nose, the object is dislodged from the breathing passage of the choking victim.

Figure 1:
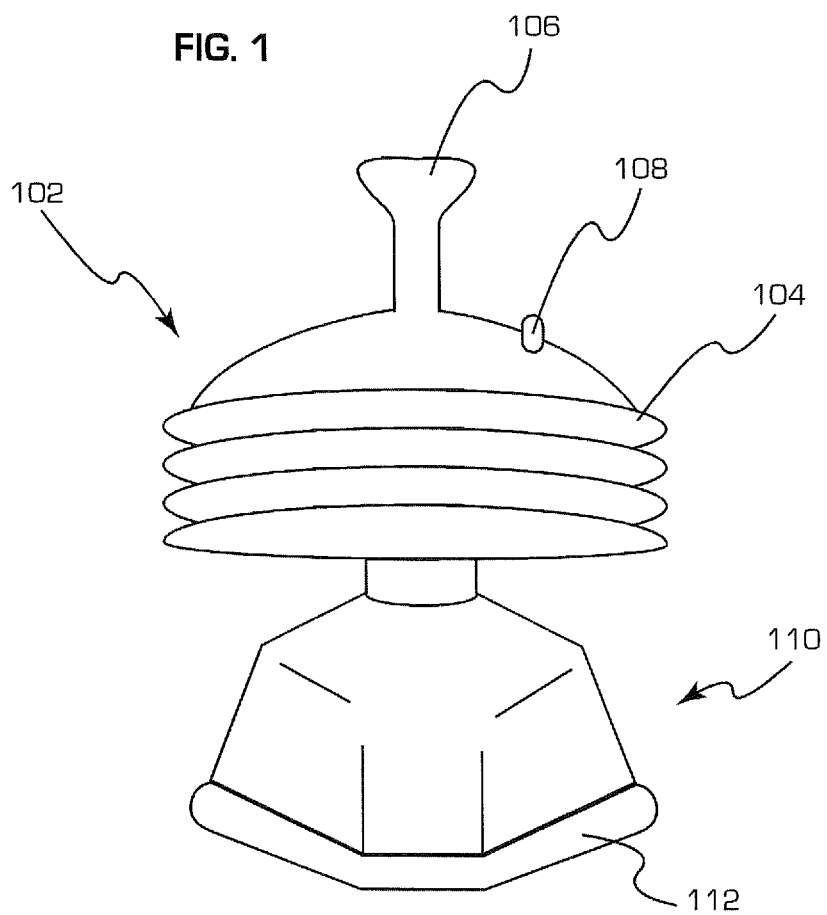
FIG. 1 illustrates a side view of an exemplary embodiment of a choking intervention device.

FIG. 1 illustrates a side view of an exemplary choking intervention device. The choking intervention device of FIG. 1 comprises a bellows assembly 102 that is configured to sealingly couple to a facemask 110. The bellows assembly 102 may have a plunger shape that includes a bellows 104 and a handle 106 disposed on a top portion of the bellows assembly 102 at a side opposite the base 114.

The bellows assembly 102 may include a relief valve 108 configured to allow air to escape from the bellows assembly 102 when the bellows 104 is being compressed. Thus, the relief valve 108 prevents substantial pressure to be built inside the bellows assembly 102 when the bellows 104 is compressed (while the bellows assembly is sealingly coupled to the facemask and the facemask is positioned over the victim's mouth and nose). The relief valve 108 is unidirectional in that it allows air to escape during compression but prevents air from escaping during suction.

In one embodiment the relief valve 108 is positioned between the handle 106 and the bellows 104, as illustrated in FIG. 1. In various implementations, the relief valve 108 is positioned on the distal end of the handle 106 or on a base 114 of the bellows 104. The handle 108 portion of the bellows assembly 102 may be ergonomically shaped in that its distal end is wider than its proximal end with respect to the bellows 104. In one embodiment, the bellows assembly 102 is a single piece made via injection mold.

In one embodiment, the facemask 110 includes a seal 112, such as a gasket or other appropriate device capable of forming a seal between a person's face and the facemask 110 when the facemask 110 is placed over the person's mouth and nose. The facemask 110 has a connector 118 (shown in FIG. 3) at an end opposite to the seal 112, wherein the connector 118 is configured to allow the facemask 110 to removably connect to the bellows assembly 102. In various implementations, the facemask 110 may be of plastic or of the same material as the bellows assembly 102. In one embodiment, both the bellows assembly 102 and the facemask 110 are a single piece made via injection mold.

Figure 2:
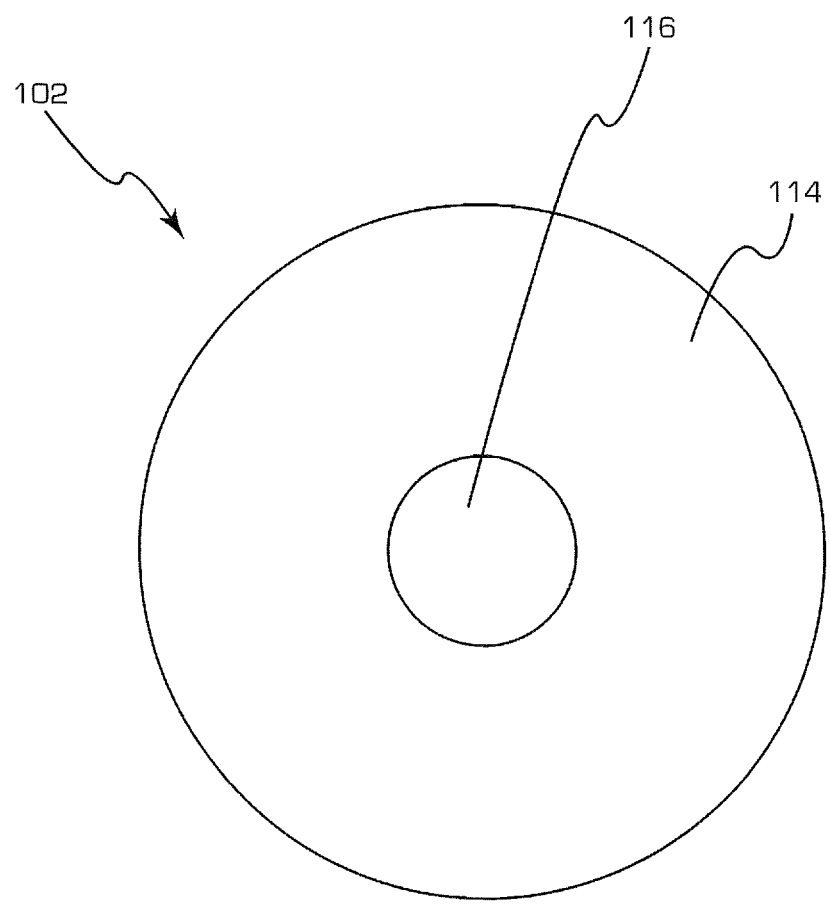
FIG. 2 illustrates a plan view of the underside of the bellows assembly of the exemplary embodiment of FIG. 1.

When the facemask 110 joins the bellows assembly 102, connector 118 creates a tight seal around the opening 116 of the base of the bellows 114. To that end, the connector 118 of the facemask 110 is configured and dimensioned to insert into the opening 116 (shown in FIG. 2) formed through the base 114 of the bellows 104. When the connector 118 is inserted and properly seated in the (e.g., circular) opening 116, a substantially airtight seal is formed between the connector 118 and the base 114. In one embodiment, a (e.g., rubber gasket) on the perimeter of the opening 116 further facilitates the seal between the connector 118 and the base 114.

It will be understood that to effectively prevent obstructions during choking, it would be advantageous for a choking intervention device to be affordable, sanitary, and/or ubiquitous (e.g., readily available). In this regard, in one embodiment, the facemask 110 portion of the present disclosure is a disposable and/or replaceable item. As an additional benefit, the choking intervention device of this exemplary embodiment avoids spreading infections between users.

While the facemask portion 110 may be configured as a "one size fits all" (e.g., universal size), in one embodiment, the facemask 110 may be dimensioned in discrete sizes (e.g., small, medium, large, extra-large) to better accommodate the mouth and nose of the choking victim (e.g., configured for different age groups). For example, a choking intervention device kit may include the bellows assembly 102 and multiple face masks 110, with at least one face mask 110 dimensioned for an adult and at least one for use on a child and/or infant choking victim. The different sized facemasks 110 are configured to provide a better seal to be formed and maintained between the victim's face and the seal 112 of the facemask 110.

In one embodiment, the bellows assembly 102 is configured to be in a collapsed form when at rest (e.g., not in use). During a choking emergency, a user of the choking intervention device may place the facemask 110, attached to the collapsed bellows assembly 102, over the choking victim's mouth and nose, thereby creating a sealed chamber between the bellows assembly 102, facemask 110, and the victim. A force is exerted on the bellows assembly in an expansion direction by pulling the handle 106 away from the choking victim. The suction generated by the expansion of the bellows 104 is operative to dislodge a foreign object obstructing the choking victim's respiratory tract such as to allow sufficient airflow to the lungs. A pressure differential created within the throat and esophagus causes the lodged object to be dislodged and sucked through the facemask 112.

Alternatively, the bellows assembly 102 may be configured to be in an extended state when at rest. In this configuration a user of the choking intervention device may place the facemask 110, attached to the bellows assembly 102, over the choking victim's mouth and nose, and exert force on the bellows assembly in a compression direction by pushing the handle 106 towards the choking victim. The relief valve 108 prevents air from being pushed into the respiratory tract of the choking victim. Once the bellows 104 is (e.g., substantially) compressed, the user provides force on the bellows assembly 102 in an expansion direction by pulling the handle 106 away from the choking victim. The suction generated by the expansion of the bellows 104 is intended to dislodge a foreign object obstructing the choking victim's respiratory tract sufficiently to allow sufficient airflow to the lungs.

During the choking intervention, several iterations of the above-described procedures may be applied to dislodge the foreign object. In both above-described configurations of the bellows assembly 102 the relief valve 108 prevents air from being pushed into the respiratory tract of the choking victim during compression of the bellows 104. Thus, the relief valve prevents further lodging the foreign object in the respiratory tract during the intervention.

The duration of the suction is short, typically less than one second. The suction power of the bellows assembly 102 is approximately three times stronger than the choke pressure of the obstruction. However, the volume of the air removed is minimal. Thus, damage to the lungs of the victim is not of immediate concern.

Figure 3:
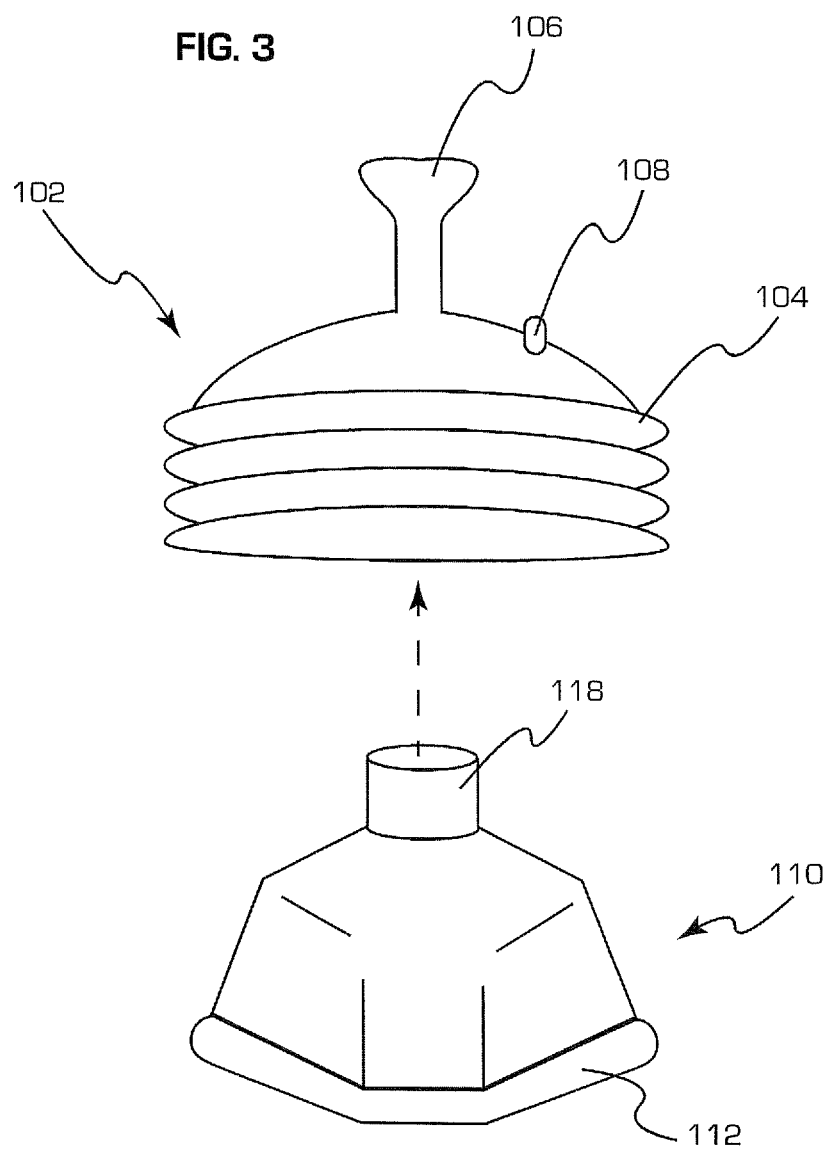
FIG. 3 illustrates an exploded view of the exemplary choking intervention device of FIG. 1.

As shown in the embodiments of FIGS. 1 and 3, the relief valve 108 may be positioned on a surface of the bellows assembly. While the relief valve 108 is shown on a top surface of the bellows 404, the illustration is a non-limiting example. Thus the relief valve 108 may be positioned at any suitable location on the bellows assembly 102, such as the base 114 of the bellows assembly 102, top of the handle 106, etc.

Figure 4:
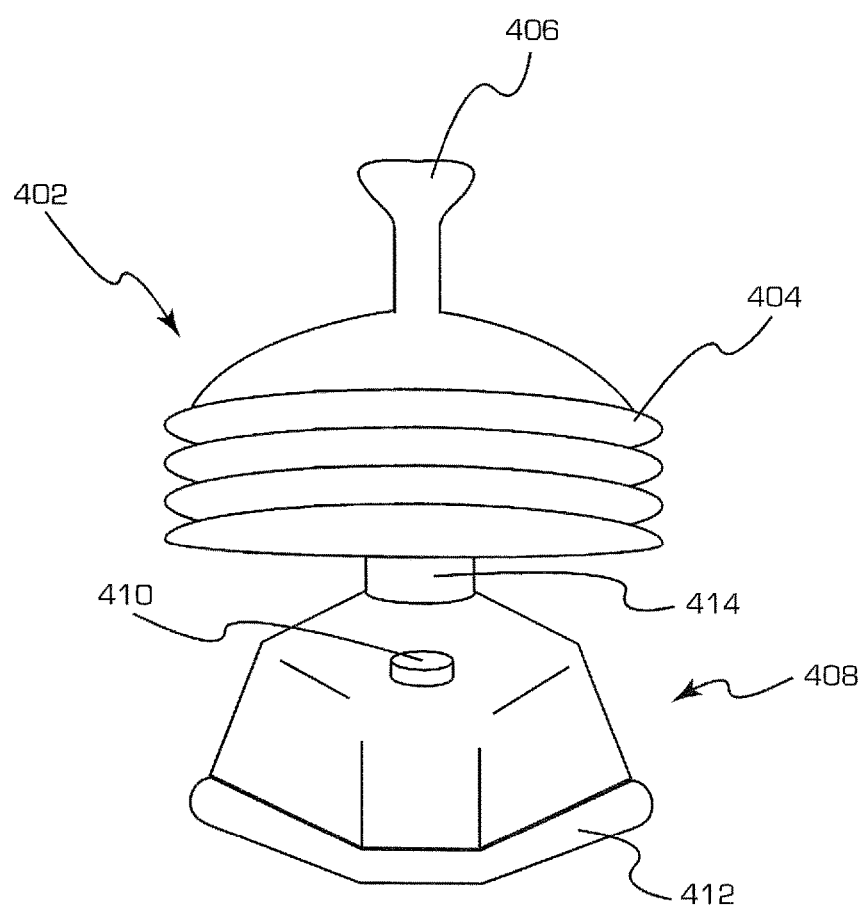
FIG. 4 illustrates another exemplary embodiment of a choking intervention device.

FIG. 4 illustrates another exemplary embodiment of a choking intervention device, where a relief valve 410 is positioned on a facemask 408 (in addition to or instead of the relief valve on the bellows assembly discussed in the context of FIG. 1). In the example of FIG. 4, the choking intervention device includes a bellows assembly 402 and a facemask 408. The bellows assembly 402 has a bellows 404 and a handle 406 disposed on a top surface of the bellows 404.

In one embodiment, the facemask 408 includes a seal 412, such as a gasket or other appropriate device capable of forming a seal between a person's face and the facemask 408 when the facemask 408 is placed over the person's mouth and nose. Additionally, the facemask 408 has the relief valve 410 positioned thereon to allow air to escape from the facemask 408 when the bellows 404 is compressed. A connector 414 fixedly coupled to the facemask 408 is configured to allow the facemask 408 to removably connect to the bellows assembly 402 in a similar manner as described in the context of the discussion of FIG. 1 above. When the connector 414 is inserted and slidingly seated in the opening of the base of the bellows, a substantially airtight seal is formed between the connector 414 and the base 114 of the bellows, thereby sealingly unifying the bellows assembly 402 with the facemask 408.

While the relief valve 410 is shown at a particular position on the facemask 408, the illustration is provided as a non-limiting example only. Thus, the relief valve 410 may be positioned at any suitable location on the facemask 408. In one example, the relief valve is positioned on the connector 414.

The embodiments discussed herein provide a choking intervention device that is light and portable. Unlike prior art devices, the embodiments described herein do not require any mounting of the device. Since there are no mounting requirements to a support structure (e.g., a table), the device can be stored at a convenient location in the home, at the office, in the glove compartment of a vehicle, included in a picnic basket, etc. Further, since the choking intervention device is not piston driven, it does not require seals, which may degrade over time. In this regard, the device may be stored for decades and still perform reliably in a choking emergency situation. The overall simplicity of the design not only keeps production costs low but makes the device reliable and affordable.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as separately claimed subject matter.

What is claimed is:

1. A choking intervention device, comprising:
   a bellows assembly configured to clear an object obstructing a breathing passage of a choking victim comprising:
   a bellows having a base with an opening configured to provide an access to an interior volume of the bellows assembly;
   a handle provided on the bellows at a side opposite the base;
   a facemask coupled to the base of the bellows and configured to enclose the choking victim's mouth and nose; and
   at least one relief valve configured to allow air to escape from inside the bellows assembly when the bellows is compressed and prevent air from entering the bellows assembly when the bellows is expanded;
   wherein the at least one relief valve is disposed on at least one of the bellows assembly, and the facemask.

2. The device of claim 1, wherein the facemask further comprises a seal configured to provide a seal between the facemask and a face of the victim when the facemask is placed over the choking victim's mouth and nose.

3. The device of claim 1, wherein the facemask further comprises a connector configured to: slidingly insert into the opening on the base of the bellows; and provide fluid communication between the interior volume of the bellows and the facemask.

4. The device of claim 1, wherein the bellows assembly and the facemask are injection molded together using a single piece of polymer.

5. The device of claim 3, wherein the bellows assembly and the facemask are two separate pieces and the facemask is removable from the bellows assembly between the opening and the connector.

6. The device of claim 5, wherein the bellows assembly is configured to couple to different size face masks.

7. The device of claim 1, wherein the facemask is configured to be of universal size.

8. The device of claim 1, wherein the bellows is configured to be compressed when the handle is pushed towards the victim's mouth and nose.

9. The device of claim 8, wherein the bellows is configured to expand and create a pressure differential between a throat and an esophagus of the victim when the handle is pulled away from the victim's mouth and nose.

10. The device of claim 1, wherein the device is portable and not mounted.

11. The device of claim 1, wherein the device is configured to be used by the choking victim.

12. A choking intervention device, comprising:
    a bellows assembly configured to clear an object obstructing a breathing passage of a choking victim, comprising:
    a bellows having a base with an opening configured to provide an access to an interior volume of the bellows assembly and dimensioned to be attached to a facemask via a facemask connector;
    a handle provided on the bellows at a side opposite the base; and,
    a relief valve configured, when the facemask is positioned over a person's mouth and nose, to allow air to escape from inside the bellows assembly when the bellows is compressed from movement of the handle toward the opening of the bellows and prevent air from entering the bellows assembly when the bellows expands from movement of the handle away from the opening of the bellows;
    wherein the relief valve is disposed on at least one of the bellows assembly, and the facemask.

13. The bellows assembly of claim 12, wherein the facemask further comprises a seal configured to provide a seal between the facemask and a face of the victim when the facemask is placed over the choking victim's mouth and nose.

14. The bellows assembly of claim 12, wherein the facemask further comprises a connector configured to: slidingly insert into the opening on the base of the bellows; and provide fluid communication between the interior volume of the bellows and the facemask.

15. The bellows assembly of claim 14, wherein the bellows assembly and the facemask are two separate pieces and the facemask is removable from the bellows assembly between the opening and the connector.

16. The bellows assembly of claim 15, wherein the bellows assembly is configured to couple to different size face masks.

17. The bellows assembly of claim 12, wherein the bellows assembly and the facemask are injection molded together using a single piece of polymer configured via injection molding.

18. The bellows assembly of claim 12, wherein the facemask is configured to be of universal size.

* * * * *